United States Patent [19]
Jervis et al.

[11] Patent Number: 5,871,498
[45] Date of Patent: *Feb. 16, 1999

[54] EXPANSIBLE APPARATUS WITH BACK-LOADED CANNULA

[75] Inventors: James E. Jervis, Atherton; Helmut Kayan, Redwood City, both of Calif.

[73] Assignee: General Surgical Innovations, Inc., Palo Alto, Calif.

[ * ] Notice: The term of this patent shall not extend beyond the expiration date of Pat. No. 5,496,345.

[21] Appl. No.: 717,794

[22] Filed: Sep. 23, 1996

[51] Int. Cl.$^6$ ..................................... A61B 19/00
[52] U.S. Cl. .............................. 606/192; 606/108; 604/96
[58] Field of Search ................................ 606/192, 1, 108, 606/151, 119; 604/96, 104, 164

[56] References Cited

U.S. PATENT DOCUMENTS

| | | | |
|---|---|---|---|
| 5,496,345 | 3/1996 | Kieturakis et al. | 606/192 |
| 5,653,726 | 8/1997 | Kieturakis | 606/192 |

*Primary Examiner*—Michael Buiz
*Assistant Examiner*—Kevin Truong
*Attorney, Agent, or Firm*—Lyon & Lyon LLP

[57] ABSTRACT

The present invention relates to an expansible tunneling apparatus suitable for tissue dissection. The apparatus is provided with a cannula-loading shaft at its proximal end such that a cannula chosen from a range of different cannulas may be loaded over the cannula-loading shaft and installed in an anatomic space created by the expansible tunneling apparatus. The apparatus is also provided with an inflatable member such as a balloon to accomplish the dissection and a sleeve covering the balloon which are removed from the apparatus before the cannula is loaded on the cannula loading shaft.

8 Claims, 5 Drawing Sheets

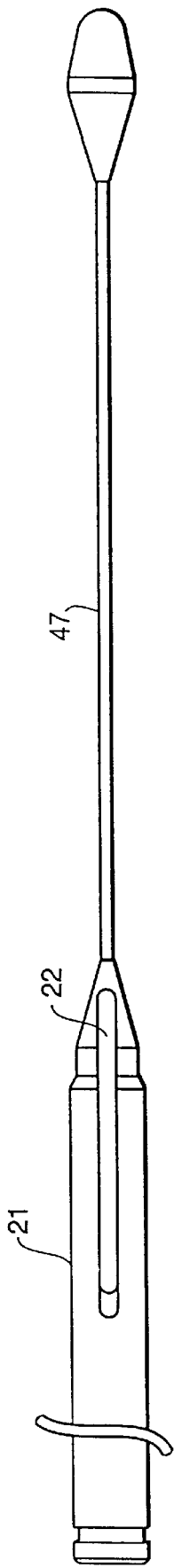
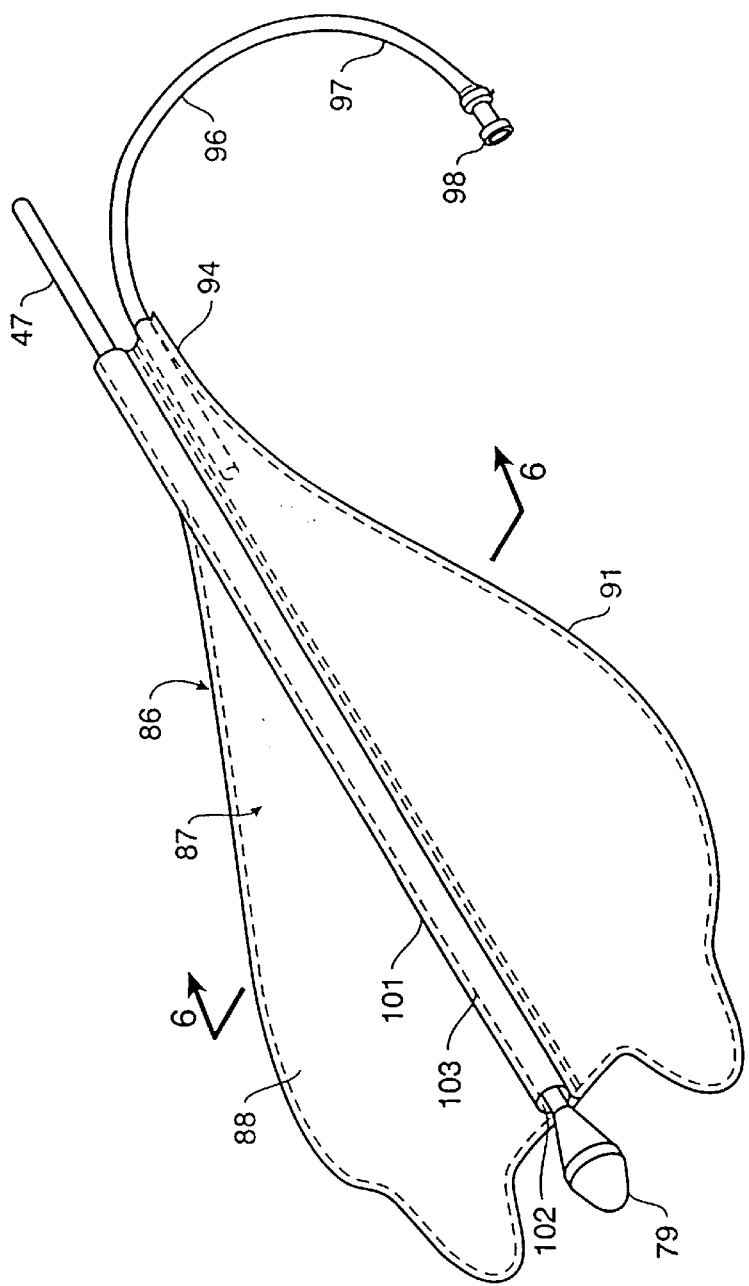
FIG. 4
FIG. 5

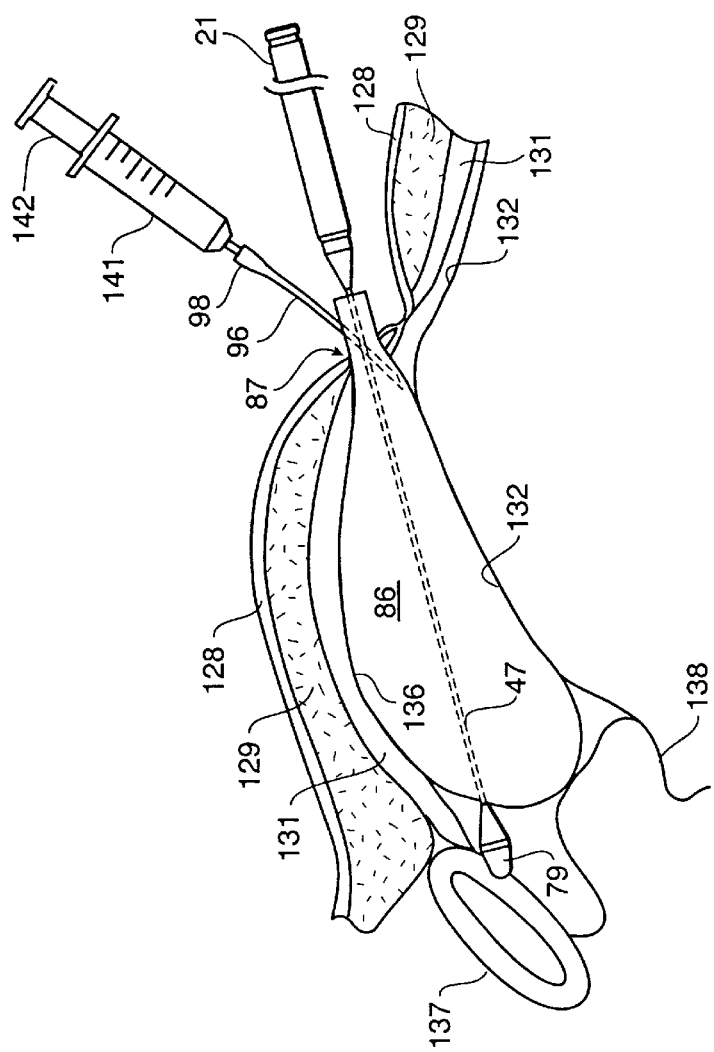
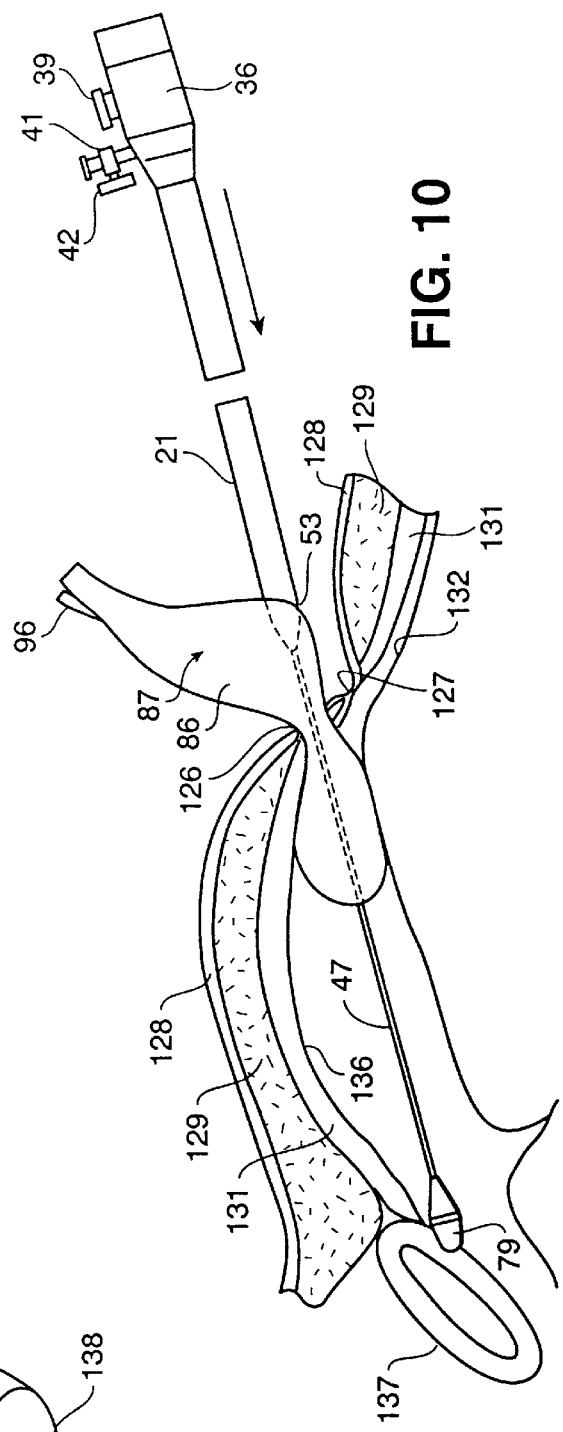

5,871,498

1

EXPANSIBLE APPARATUS WITH BACK-LOADED CANNULA

BACKGROUND OF THE INVENTION

This invention relates to an apparatus and method for facilitating the installation of one of a range of different cannulas according to a medical practitioner's choice, over an expansible tunneling apparatus.

Devices of the general type disclosed in U.S. Pat. No. 5,496,345, which is owned by the Assignee of the present application and which is incorporated in its entirety herein by reference, have been used to achieve excellent results in actual use and, generally, comprise a tunneling member having an expansible device such as a balloon attached to the tunneling member which can be used for tissue dissection. When the tunneling member is used in its preferred mode, an incision is first made to gain access to a natural tissue plane and the tunneling device is introduced and tunnels a path between layers of tissue lying generally parallel to each other along a natural tissue plane. The balloon is then inflated to dissect tissue along the natural tissue plane and an anatomic working space which did not previously exist is created so that surgical or other medical procedures can be performed. Such procedures are more fully described in U.S. Pat. No. 5,496,345.

However, devices of this type presently in use have a bulky proximal end and a captive cannula assembled distally of this proximal end. In practice therefore, it is not possible to exchange cannulas to obtain alternative features without complete removal of the devices. This risks losing access to working space created since the distal end of the device, which maintains a path to the space, must be removed.

In general, it is an object of the present invention to provide an apparatus and method which allow a choice of cannulas after the working space is created and which is simpler for the medical practitioner to use.

SUMMARY OF THE INVENTION

The device of the present invention comprises an expansible tunneling apparatus in which a balloon is mounted on a tunneling shaft or rod, the distal end of which is provided with a blunt member which is preferably configured so as to facilitate tunneling. The tunneling shaft is connected to a proximal cannula-loading shaft over which a cannula may be installed. The balloon is provided with means for inflating the balloon and a removable sleeve is installed over the balloon on the tunneling shaft to gather the balloon about the shaft.

In use, the tunneling device may first be used to tunnel along a natural tissue plane to a desired location. The removable sleeve is then removed, freeing the balloon to expand upon being inflated with a suitable medium, e.g., saline solution or air. In such use, the inflation of the balloon causes dissection between tissue layers along a natural tissue plane to form an anatomic space. The balloon, which is removably attached to the tunneling shaft may then be deflated and removed from the tunneling shaft and from the anatomic space such that only the tunneling shaft and the cannula-loading shaft remain.

A cannula of any suitable type can be used, e.g., one with a flapper valve capable of manual operation such as the Ethicon Endopath cannula, which will fit over the cannula loading shaft, the diameter of which tunneling shaft is chosen to facilitate loading of a desired range of available cannulas, and which can be advanced so that the cannula extends into the anatomic space created by the tunneling apparatus. If equipped with a skinseal, the cannula can be made to seal the incision originally made. The tunneling apparatus comprising the cannula loading shaft and tunneling shaft, can then be removed proximally through the cannula which is typically provided with valve means to prevent leakage of body fluids.

BRIEF DESCRIPTION OF THE DRAWINGS

FIG. 4 is a side view of the cannula loading shaft showing a groove in which the inflation tube for the balloon is held.

FIG. 5 is an isometric view of the inflatable balloon attached to the tunneling shaft.

FIG. 9 is a view similar to FIG. 8, but showing the removable sleeve removed from the apparatus and the balloon inflated.

FIG. 10 is a sagittal view similar to FIG. 8, but showing the deflated balloon being removed. This figure also shows how a cannula may be loaded on the cannula loading shaft.

DETAILED DESCRIPTION OF THE PREFERRED EMBODIMENTS

The apparatus of the present invention is suited for use in the general manner shown and disclosed in U.S. Pat. No. 5,496,345, which is incorporated by reference herein. However, there are important differences in device capability and utility for the apparatus of the present invention.

Figure 1:
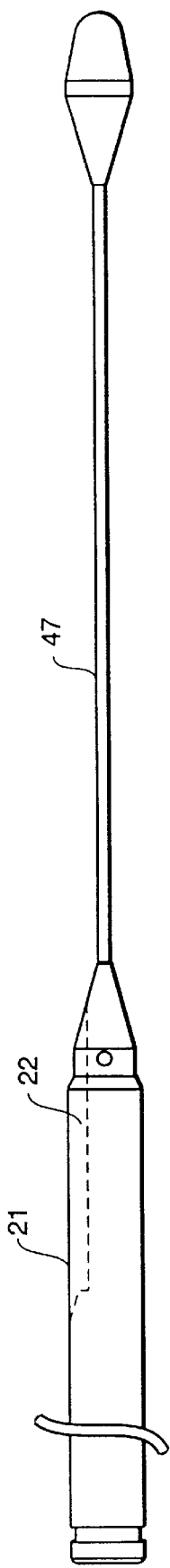
FIG. 1 is a side view of the tunneling shaft and cannula-loading shaft prior to attachment of the balloon.

As shown in FIG. 1, the tunneling device 20 of the present invention, prior to installation of the balloon and removable sleeve, comprises a tunneling shaft 47 having a tunneling tip 79 at its distal end and a cannula loading shaft 21 attached to the proximal end of the tunneling shaft. The distal end of the cannula loading shaft is preferably tapered or conical.

Figure 2:
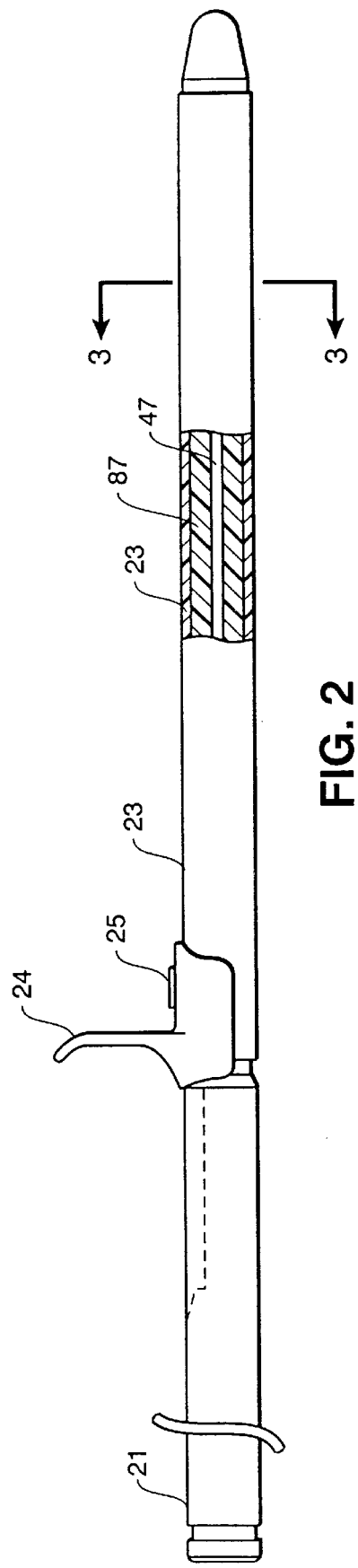
FIG. 2 shows, in partial cross-section, the device of the present invention with the balloon attached to the tunneling shaft and the removable sleeve surrounding the balloon.
Figure 3:
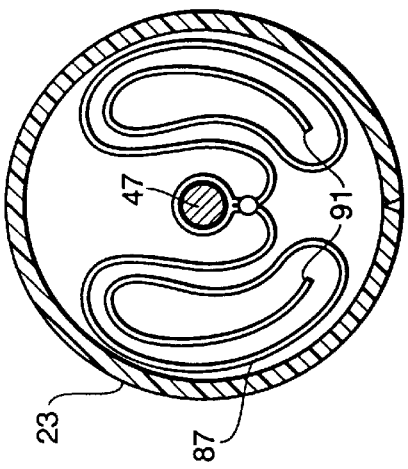
FIG. 3 is a cross-sectional view taken along the line 3—3 of FIG. 2.

FIG. 2 shows a balloon assembly 86 including balloon 87 installed on tunneling shaft 47 as does FIG. 3. FIG. 2 also shows removable sleeve assembly 23 installed over balloon 87 and shows that removable sleeve assembly 23 is provided with handle 24. Handle 24 is attached to removable sleeve 23 by clip 25.

FIG. 4 shows cannula loading shaft 21 (with tunneling shaft 47) and also shows balloon holding groove 22 which is used to engage flexible tubular member 96 attached to balloon 87. Groove 22 is also shown in FIG. 1. Groove 22 is sized such that it will releasably engage tubular member 96, e.g., by having a width which is somewhat smaller than the diameter of tubular member 96 to hold balloon 87 in place when removable sleeve 23 is withdrawn. The same result may be achieved by adding a widened portion to tubular member 96, e.g., a thickened weld at the point where tubular member 96 and balloon 87 overlap.

As shown in FIG. 5, the balloon 87 may have a generally pear-shaped configuration when deflated. Balloon 87 is preferably formed of a non-elastomeric, medical grade material of a suitable type such as polyvinyl chloride or polyurethane. Balloon 87 can be formed of two sheets, 88 and 89, of such material which have their outer margins bonded together by suitable means such as by heat at margin 91 extending around the perimeter of balloon 87.

Balloon 87 may also be a single molded piece.

Balloon 87 is also provided with a neck 94 into which a flexible tubular member 96 extends. Tubular member 96 is secured to balloon 87 in a suitable air tight fashion, such as by an adhesive. The tubular member 96 is provided with a lumen 97 which is in communication with the interior of the balloon 87 and which can be used for inflating balloon 87 through a Luer-type fitting 98 mounted on the free end member 96.

Means are provided for removably securing balloon 87 to tunneling shaft 47 such as by sleeve 101 formed of the same material as balloon 87, and which can be formed integral or separate therefrom and adhered thereto by suitable means such as an adhesive. The sleeve 101 extends longitudinally of the balloon 87 and is disposed generally equidistant from the side margins thereof. The sleeve 101 is provided with passage 102 extending therethrough which is sized to slidably accommodate the tunneling shaft 47. Means are provided for permitting separation of balloon 87 from the tunneling shaft 47 and may take the form of longitudinally spaced apart perforations 103 in sleeve 101 extending along sleeve 101. Perforations 103 are spaced closely enough together to form a weakened region so that the balloon can be readily separated from tunneling shaft 47 by tearing along perforations 103 in sleeve 101. The distal portion of sleeve 101 can be provided with means, e.g., a radially extending ridge, which will create a tighter fit with shaft 47 and inhibit axial movement of balloon 87 when removable sleeve 23 is withdrawn.

Figure 6:
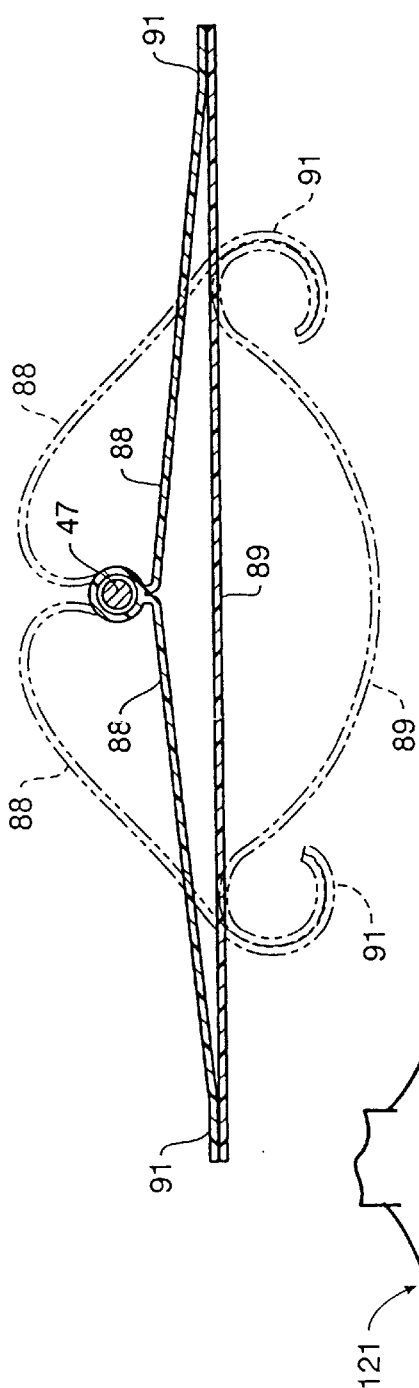
FIG. 6 is a cross-sectional view taken along the line 6—6 of FIG. 5 and showing by dotted lines the manner in which the balloon unfolds from its original rolled up position as shown in FIG. 3.

As shown in FIG. 6, sleeve 101 may be disposed equidistant from the side margins of balloon 87 facilitating the inflation of balloon 87. When deflated, the side margins of the balloon 87 can be rolled inwardly toward tunneling shaft 47 as shown by the broken lines in FIG. 6 to permit the same to be folded into the configuration shown in FIG. 3. In this configuration, balloon 87 can be enclosed within removable sleeve 23 which comprises a cylindrical tube with a weakened region, e.g., a longitudinal groove in its wall, as shown in FIG. 3. Removable sleeve 23 is formed of a relatively thin-walled tubular material such as Teflon or polyethylene. Instead of being provided with a longitudinal groove, the removable sleeve could take the form of a tube simply split along its length or a tube having perforations or slots formed in its wall, or a combination thereof. Alternatively, the removable sleeve could be made integral with the balloon and made out of the balloon material such that a separate removable sleeve, such as sleeve 23, shown in the drawings, would be unnecessary.

The proximal extremity of tubular sleeve assembly 23 is provided with handle 24 attached to sleeve 23 by clip 25. Handle 24 is operable by the application of moderate pressure, as with finger or hand, to facilitate the separation of sleeve 23 so as to remove it from the device and so as to leave balloon 87 free to inflate and expand.

Figure 8:
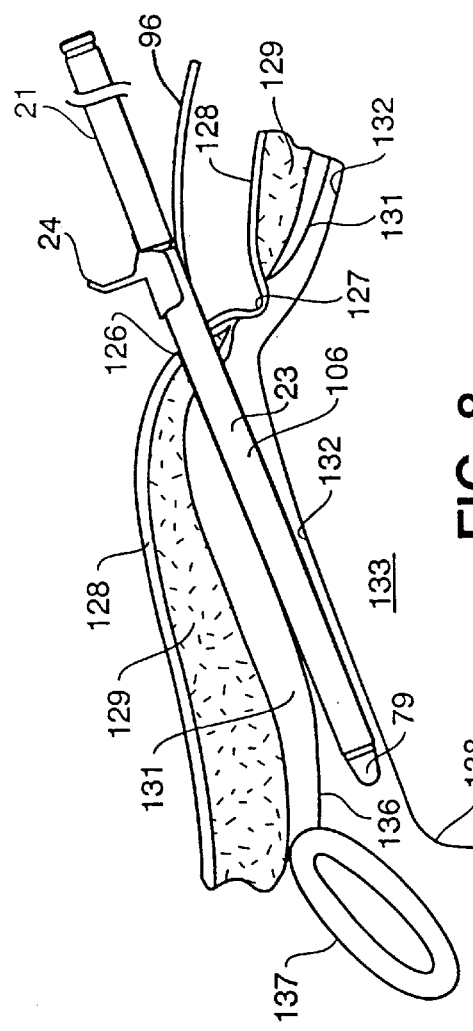
FIG. 8 is a sagittal view of the lower abdominal cavity of the human being shown in FIG. 7 and showing the apparatus of the present invention introduced into the pre-peritoneal space.

The apparatus of the present invention can be used as follows: to perform a hernia repair procedure. For example, if a human patient 121, as figuratively shown in FIG. 7, has a hernia 122 in the lower abdominal area, the patient may be prepared in an appropriate manner by administering a suitable anesthesia and any other preparation deemed appropriate. As shown in FIG. 8, the surgeon may first make an infraumbilical incision 126 in the skin below the navel or umbilicus 127 which first separates the fat 129 and then incises the anterior rectus sheath or fascia 131 and the rectus muscle near the midline. Care should be taken not to penetrate the peritoneum 132 overlying the abdominal cavity 133.

Using the cannula loading shaft 21 as a handle, tunneling tip 79 of the device of the present invention is then inserted into incision 126 and caused to advance by the surgeon towards the pubic region of the patient, anterior to the peritoneum, while the surgeon places his other hand on the abdomen to feel the advance of the tunneling apparatus. This advance is continued until the tunneling tip 79 is below the symphysis pubis 137 as shown in FIG. 8, and preferably between the symphysis 137 and the bladder 138.

After the device of the present invention has been properly positioned as shown in FIG. 8, the removable sleeve 23 is removed by using handle 24 to pull the sleeve out of the incision and to cause the weakened portion of the removable sleeve to separate such that the sleeve can be removed from the balloon and from the patient's body. As the removable sleeve 23 opens and slips off, it exposes balloon 87. When removable sleeve 23 is completely removed, balloon 87 is inflated, e.g., by introducing a suitable inflation medium such as a sterile saline solution through, as shown in FIG. 9, tubular member 96. This is accomplished by connecting a conventional syringe 141 to the Luer-fitting 98 attached to tubular member 96. Balloon 87 can typically be inflated to a suitable size by introducing 500 cc or less of normal saline solution into the balloon 87 by pressing on plunger 142 of syringe 141. As balloon 87 is inflated, it progressively unwraps with its side margins rolling outwardly from the center while expanding into a plane to cause progressive dissection of tissue, i.e., dissection of tissue layer 131 from tissue layer 132 by application of forces generally perpendicular to the plane of the balloon 87 so as to create a pre-peritoneal anatomic space. The progressive expansion of balloon 87 is shown by the dotted lines in FIG. 6. The surgeon can sense the filling of the balloon 87 by feeling the abdomen of the patient. By using a nonelastomeric material to fabricate balloon 87, working spaces of predetermined shape may be created. Different sizes or shapes of balloons can be utilized for different patient sizes and for different procedures other than hernia repair. When the balloon is of suitable size and shape, it can be deflated and shifted to a further location and again reinflated to create a larger anatomic space.

Referring now to FIG. 10, the balloon can be deflated, e.g., by withdrawal of the plunger 142 of syringe 141 or by other suitable means such as a hospital vacuum aspirator (not shown). After balloon 87 has been deflated, it can be removed by grasping the cannula-loading shaft 21 in one hand and the tubular member 96 and the proximal extremity of balloon 87 in the other hand and then pulling balloon 87 through incision 126, as shown in FIG. 10. The shaft is held in pace as balloon 87 is being removed.

Balloon 87 is progressively freed from the tunneling shaft 47 by causing sleeve 101 to split apart along longitudinal perforations 103 provided in sleeve 101. This makes it possible to separate balloon 87 from tunneling shaft 47 without removing tunneling shaft 47. After balloon 87 has been removed, the geometry of the cannula loading shaft 21 makes it possible to pass a cannula 36 over cannula-loading shaft 21 until its distal tubular end 33 extends substantially into anatomic space 136 which was created by inflation of the balloon 87. The cannula-loading shaft 21 and tunneling shaft 47 may then be removed from the incision by withdrawing them through the lumen in cannula 36. Typically, cannula 36 will be provided with a valve which permits passage of the cannula-loading shaft 21 through the lumen of the cannula and out of the cannula.

Figure 7:
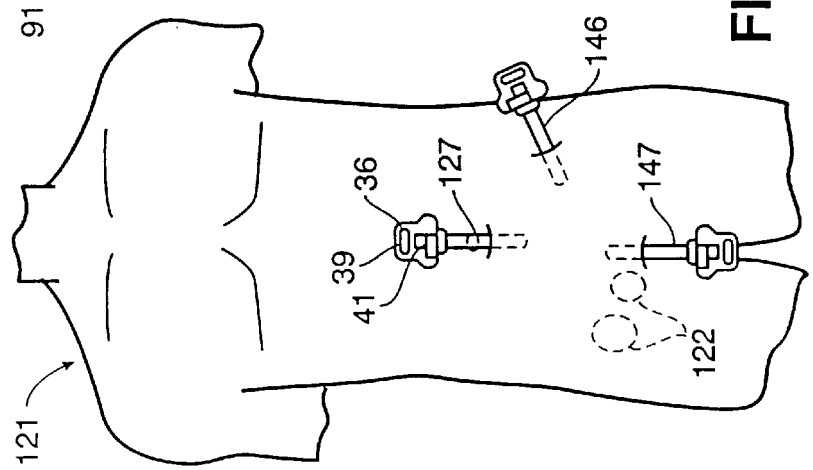
FIG. 7 is a partial view of a prone human body, showing the lower abdomen and the manner in which the apparatus of the present invention can be utilized for performing a hernia repair through the pre-peritoneal space.
Figure 11:
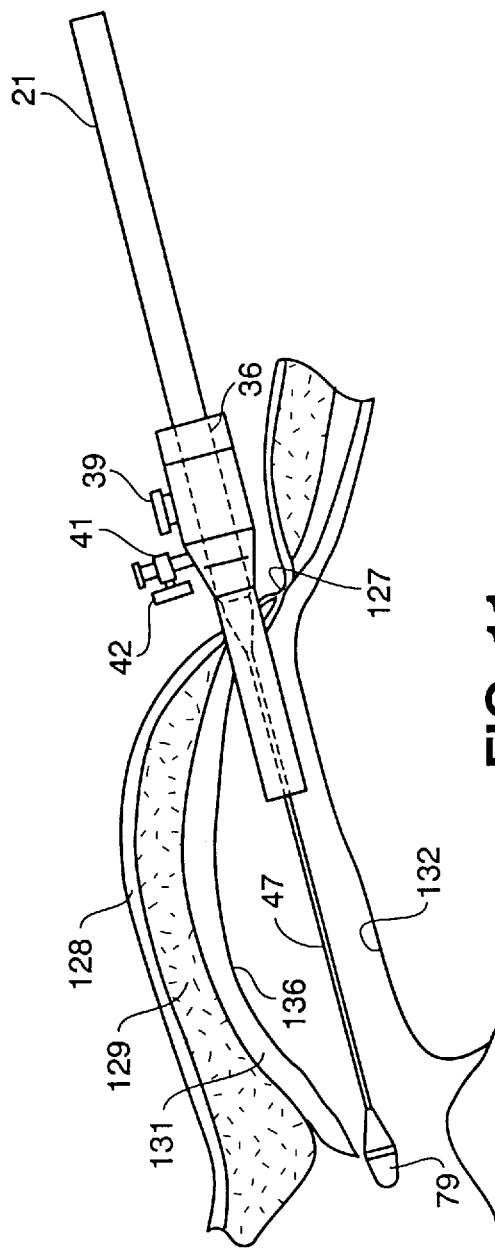
FIG. 11 is similar to FIG. 10 and shows the cannula loaded on the cannula shaft and before removal of the tunneling shaft and cannula loading shaft through the cannula lumen.

Upon removal of the cannula loading shaft 21 and tunneling shaft 47 through and out of the cannula, the valve generally closes to prevent any leakage through the cannula. The dissected pre-peritoneal space 136 is then insulated, e.g., with carbon dioxide, through stopcock 41 to a typical pressure ranging from 6 to 8 millimeters of mercury. Thereafter, as shown in FIG. 7, additional trocars, e.g., 146 and 147, are introduced through the abdominal wall into the dissected preperitoneal space 136 immediately above the symphysis pubis 137 and directly below the cannula 36. The location of any such trocars 146 and 147 will, of course, be generally dictated by the location of the hernia 122 to be repaired and by surgical preference. Thereafter, the hernia can be repaired, e.g., in the manner disclosed in U.S. Pat. No. 5,496,345 which is incorporated herein by reference.

It is to be understood that the present invention is not limited to the foregoing specific embodiment. For example, the balloon 87 may have a variety of shapes including spherical, ovoid, toroidal, etc., and may be to facilitate surgical or other procedures in various locations in the body. The variety of cannulas which may be loaded and unloaded over the cannula loading shaft is greatly increased, provided that the diameter of the cannula loading shaft 21 is sized to accommodate the lumen size of the cannula. For example, cannulas of different length, diameter, skin seal type and/or valving may be selected depending upon the particular use to which the expansible tunneling apparatus is to be put. The device of the present invention is easy to use and requires only a modest amount of training before it can be put to effective use.

Furthermore, the cannula-loading shaft and the tunneling shaft of the device of the present invention may be constructed such that the cannula-loading device is slidably, rather than fixedly, mounted on the tunneling shaft. When this alternative embodiment is used, the tunneling shaft is preferably provided with a means, e.g., a radially extending tab, which will interact with means on the cannula-loading shaft, e.g., a slot, to limit the range of longitudinal movement of the cannula-loading shaft over the tunneling shaft. In addition, in such construction, a locking means, e.g., a docking slot in the cannula-loading shaft for the tab on the tunneling shaft may be provided adjacent to the distal portion of the longitudinal slot in which the tab rides. Thus, locking may be accomplished by rotational movement of the cannula loading shaft and/or the tunneling shaft to cause the tab to be displaced laterally from the longitudinal slot to the docking slot, the longitudinal length of the latter being preferably only slightly longer than the longitudinal dimension of the tab. This sliding relationship between the cannula loading shaft and the tunneling shaft makes it possible, after the removable sleeve and balloon have been removed from the incision, to slide the cannula-loading shaft distally over the tunneling shaft to cause the tapered or conical distal end of the cannula-loading shaft to penetrate the incision. When this is done, the installation of the cannula in the anatomic space created by the expansible tunneling apparatus is facilitated by enlargement of the incision by the cannula loading shaft which more readily accomplishes this enlargement by reason of its conical or tapered distal end.

The cannula-loading shaft can also be fabricated into two sections. In such case, the proximal section will be fixedly mounted on the tunneling shaft and the distal section will be slidably mounted on the tunneling shaft. This construction facilitates control of the tunneling shaft by means of the fixedly mounted proximal section of the cannula-loading shaft while permitting the distal section of the cannula-loading shaft to be slidably advanced over the tunneling shaft.

It is also to be understood that, once the cannula is installed in the anatomic space created by the expansible tunneling device of the present invention, the cannula can be used as an access port for an endoscope, for surgical instruments, or for such other purposes, in addition to or instead of insufflation, as the medical practitioner may desire to employ. Accordingly, the present invention is not limited to the foregoing specific examples, but is of the full scope of the claims appended hereto.

What is claimed is:

1. An assembly for creating an anatomic space comprising:
   (a) a tunneling shaft having a distal and proximal end and having a cannula-loading shaft attached to its proximal end, said cannula-loading shaft adapted to receive a lumen of a cannula and having a free proximal end unattached to any structure having a larger cross-section than the cannula-loading shaft;
   (b) a balloon removably attached to said tunneling shaft;
   (c) a means for providing inflation fluid to said balloon attached to said balloon; and
   (d) a removable sleeve substantially covering and surrounding said balloon on said tunneling shaft.

2. The assembly of claim 1 wherein a cannula is loaded on said cannula-loading shaft.

3. The assembly of claim 1 wherein at least a portion of said cannula-loading shaft is slidably mounted on said tunneling shaft.

4. The assembly of claim 1 wherein said tunneling shaft has a rounded blunt distal end.

5. The assembly of claim 1 wherein said cannula-loading shaft has a tapered distal region.

6. A method of creating an anatomic space comprising the steps of:
   (a) making an incision;
   (b) passing an expansible tunneling apparatus through said incision to a desired location, said expansible tunneling apparatus comprising a tunneling shaft having a distal and proximal end, a cannula-loading shaft attached to the proximal end of said tunneling shaft, said cannula-loading shaft free of a surrounding cannula, a balloon attached to said tunneling shaft, means for providing inflation fluid to said balloon attached to said balloon, and a removable sleeve substantially covering and surrounding said balloon on said tunneling shaft;
   (c) removing said removable sleeve;
   (d) inflating said balloon to create an anatomic space;
   (e) deflating and removing said balloon from said anatomic space;

(f) loading a cannula having a lumen on said cannula-loading shaft and advancing a distal portion of said cannula into said anatomic space; and (g) withdrawing said tunneling shaft and said cannula-loading shaft through the lumen of said cannula.

7. The method of claim 6 wherein, prior to advancing said cannula into said anatomic space, at least a portion of said cannula-loading shaft is advanced over said tunneling shaft such that a distal region of said cannula-loading shaft enters the incision.

8. The method of claim 6 further comprising the step of removing said cannula from said cannula-loading shaft.

\* \* \* \* \*

UNITED STATES PATENT AND TRADEMARK OFFICE
CERTIFICATE OF CORRECTION

PATENT NO.   : 5,871,498
DATED        : February 16, 1999
INVENTOR(S)  : Jervis, et. al.

It is certified that error appears in the above-identified patent and that said Letters Patent is hereby corrected as shown below:

In column 5, line 19, delete "insulated" and insert therefor --insufflated--.

Signed and Sealed this

Thirtieth Day of November, 1999

Attest:

Attesting Officer

Q. TODD DICKINSON

Acting Commissioner of Patents and Trademarks